United States Patent
Lee et al.

(10) Patent No.: US 8,747,940 B2
(45) Date of Patent: Jun. 10, 2014

(54) MANUFACTURING PROCESSES FOR MAKING MEDICAL DEVICES HAVING A COATING GRADIENT

(71) Applicant: Abbott Cardiovascular Systems Inc., Santa Clara, CA (US)

(72) Inventors: Jeong S. Lee, Diamond Bar, CA (US); Kenneth L. Wantink, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/749,483

(22) Filed: Jan. 24, 2013

(65) Prior Publication Data
US 2013/0136847 A1    May 30, 2013

Related U.S. Application Data

(63) Continuation-in-part of application No. 11/834,164, filed on Aug. 6, 2007.

(51) Int. Cl.
*B05D 3/02* (2006.01)
*A61M 25/00* (2006.01)
*B05D 1/32* (2006.01)

(52) U.S. Cl.
USPC ........... 427/2.28; 427/2.1; 427/259; 427/282; 604/915; 606/108

(58) Field of Classification Search
USPC ................ 427/2.28, 2.1, 2.3, 256, 259, 282; 604/915; 606/108
See application file for complete search history.

(56) References Cited

U.S. PATENT DOCUMENTS

| | | | |
|---|---|---|---|
| 6,458,138 B1 * | 10/2002 | Sydney et al. | 606/108 |
| 6,558,798 B2 * | 5/2003 | Zhong et al. | 428/420 |
| 7,184,812 B2 * | 2/2007 | Sinderby et al. | 600/393 |
| 7,544,381 B2 * | 6/2009 | Kangas | 427/2.1 |

* cited by examiner

Primary Examiner — Cachet Sellman
(74) Attorney, Agent, or Firm — Fulwider Patton LLP (57) ABSTRACT

Methods for forming a "coating gradient" on medical devices, such as a balloon catheter or guidewire are disclosed. The balloon portion of the catheter has a protective covering initially placed over it to prevent the balloon from receiving a first hydrophilic coating. After a first hydrophilic coating is applied, the protective covering is removed. A second hydrophilic coating could be applied to the catheter. A guidewire having less lubricity at the distal end portion also can be created. A first hydrophilic coating is applied to the elongated shaft and distal shaft section of the guidewire. After the first hydrophilic coating cures, the first hydrophilic coating is removed from a portion of the distal shaft section of the guidewire. A second hydrophillic coating can then be applied to the elongated shaft and distal shaft section of the guidewire. The second hydrophilic coating can be allowed to cure.

25 Claims, 5 Drawing Sheets

MANUFACTURING PROCESSES FOR MAKING MEDICAL DEVICES HAVING A COATING GRADIENT

CROSS-REFERENCES TO RELATED APPLICATIONS

This application is a Continuation-in-Part of application Ser. No. 11/834,164, filed Aug. 6, 2007, which is incorporated by reference in its entirety herein.

BACKGROUND OF THE INVENTION

This invention relates to the field of lubricious hydrophilic coatings for intracorporeal medical devices such as, for example, a catheter or guidewire.

The use of a medical devices within a patient may be facilitated by the presence of a lubricious surface on the device. For example, intravascular devices, such as catheters and guidewires, are more easily maneuvered within a patient's vasculature when the friction between the walls of the vessel and the intravascular device is reduced. The friction may be reduced by coating the device with a hydrophilic compound which becomes slippery after adsorbing an appreciable amount of water. Consequently, the hydrophilic coating provides lubricity when the coated device is exposed to aqueous solution, as when the coated device is exposed to water prior to insertion in the patient or to the patient's blood during use. Alternatively, coatings, such as fluoropolymers, and silicone, provide lubricity to the surface of an intracorporeal device without the need for exposure to aqueous solution. However, the degree of lubricity may vary greatly depending on the nature of the lubricious coating. Hydrophilic coatings provide superior lubricity compared to hydrophobic coatings, such as silicone, when tested against a biological tissue countersurface.

In addition to lowering the coefficient of friction of the coated device, an effective lubricious coating must strongly adhere to the device surface. The lubricious coating should remain adhered to the device surface during potentially extended periods of storage, as well as in response to abrasive forces encountered during use. Poor adhesive strength is undesirable because the lost coating may be left behind inside the patient during use, with a corresponding decrease in the lubricity of the device. Typically, a trade off exists between a coating's lubricity and the coating's adhesive and cohesive strength, so that attempts to increase the durability of lubricious coatings may inadvertently decrease the lubricity of the coating. Durability is particularly an issue on the surfaces of catheters and guidewires which are subjected to significant rubbing and abrasive forces as the devices are slidably advanced through the patient's tortuous vasculature. Consequently, one difficulty has been providing a highly lubricious coating with long lasting lubricity on a surface of a catheter or guidewire.

"Watermelon seeding" is a term known in the art to describe a phenomenon which can occur when the medical device is lubriciuosly coated. This term refers to slippage of the balloon wherein the balloon which is too lubricious and shoots forward upon inflation causing accidental slippage from the target or repair site which can ultimately may lead to stent slippage from the target site as well. This phenomenon has been addressed in the art by selectively coating the folded balloon so that when the balloon is being inflated, uncoated balloon sections decrease the slipperiness of the balloon surface.

In the case of a guidewire, it is advantageous to have an lubricious coating applied to the outer surface of the device as well since the coating helps to cross the often tight lesion. However, if the distal tip or distal section of the guidewire is too lubricious, there could be a loss of tactile feel to the interventional cardiologist. Still, it is desirable to have some lubricity at the distal end of the guidewire to maintain lesion crossability and control.

Therefore, it would be a significant advance to provide a highly durable hydrophilic coating on the outer surface of a medical device to render the device highly lubricious but which avoids "watermelon seeding" of the balloon catheter and the loss of tactile feel in the case of a guidewire. The present invention satisfies these and other needs.

SUMMARY OF THE INVENTION

The present invention is directed to methods for forming a "coating gradient" on a medical device, such as a balloon catheter or guidewire. In one aspect of the method of the present invention, the balloon portion of the catheter could have a protective covering initially placed over it to prevent the balloon from receiving a first hydrophilic coating. The protective coating can be, for example, an elastomeric sheath tubing which is placed over the balloon when the balloon is placed in an inflated condition. Alternatively, the protective coating could be placed over the balloon while the balloon remains in a collapsed position. After the first hydrophilic coating is applied to the catheter, the protective covering can be removed exposing the uncoated surface of the balloon. Next, after the protective covering has been removed, a second hydrophilic coating could be applied to the catheter. In this method of the present invention, the balloon will only have a single layer of hydrophilic coating opposed to the remainder of the catheter which will have a double coating of hydrophilic coating resulting greater lubricity to the portion of the catheter proximal to the balloon.

In another aspect of the present invention, a "gradient coating" can be applied onto a guidewire. This method creates a guidewire having less lubricity at the distal end portion of the guidewire than the shaft portion which extends proximally away from the distal end section. The method includes the application of a first hydrophilic coating on the elongated shaft and distal shaft section of the guidewire. The first hydrophilic coating is removed from a portion of the distal shaft section of the guidewire. In one aspect of the present invention, the first hydrophilic coating is removed from the portion of the distal shaft section by placing the portion of the distal shaft section in an isopropanol bath which is agitated ultrasonically. This first hydrophilic coating is then allowed to cure. For example, the first coating could be subjected to an ultraviolet source that helps to cure the material.

After the first coating has been removed from a portion of the distal shaft section of the guidewire and cured, a second hydrophillic coating can be applied to the elongated shaft and distal shaft section of the guidewire. Thereafter, the second hydrophilic coating can be allowed to cure. For example, the second coating also could be subjected to an ultraviolet source that helps to cure the material.

The invention is also directed to a medical device having a lubricious coating on at least a section of the medical device, In one aspect of the present invention, the lubricious coating comprising a network of a hydrophilic compound crosslinked to itself and interlocked with a network of a multifunctional polymerized compound. One aspect of the invention is a method of coating a medical device with the lubricious coating. Additional aspects of the invention are directed to including one or more agents in the coating which provide enhanced adhesion of the coating on the device, or which provide faster hydration of the coating and/or improved lubricity. Additionally, the lubricious coating can be provided with one or more therapeutic or diagnostic agents, and in one embodiment the agent elutes relatively quickly in a concentrated release from the lubricious coating upon hydration of the coating during use of the device.

In another aspect of the present invention, the lubricious coating comprises the cured reaction product of a solution mixture which is applied onto a surface of the medical device and then cured on the device. In one aspect of the present invention, the solution mixture is formed by mixing together at least the following components: a multifunctional monomer or polymer network-forming compound, a hydrophilic compound, one or more first cross-linkers for cross-linking the multifunctional monomer or polymer, and optionally one or more second cross-linkers, different than the first cross-linkers, for cross-linking the hydrophilic compound. The first cross-linkers preferentially cross-link the multifunctional monomer or polymer relative to the hydrophilic compound, and the second cross-linkers preferentially cross-link the hydrophilic compound relative to the multifunctional monomer or polymer. In a presently preferred embodiment, the network-forming compound is an oligomer during preparation of the solution mixture. However, it may alternatively be added to the solution mixture as a monomer (prepolymerization) or as a longer chain polymer, such that it may undergo a greater or lesser degree of polymerization on the device depending on whether it is added as a monomer, oligomer, or longer chain polymer. Irrespective of whether or not the network-forming compound is added to the solution mixture in the form of a monomer or a relatively low or high molecular weight polymer, it should be understood that the multifunctional monomer or polymer of the solution mixture is in a polymerized state in the finished coating on the device when cured.

The cross-linkers are preferably photo cross-linkers which initiate the cross-linking reactions in response to irradiation with light (e.g., of the ultraviolet or visible wavelengths). However, thermal initiators, such as peroxides, which respond to increased temperature could be used in an alternative embodiment. Thus, although discussed below primarily in terms of the preferred photo cross-linkers for photo-curing the coating, it should be understood that alternative embodiments may include one or more alternative initiators which react by other mechanisms. The terminology photo cross-linkers should be understood to refer to compounds that work by various mechanisms to cause the network-forming cross-linking, including cross-linking agents that become incorporated into the network, or alternatively, photoinitiators that form radicals that result in the cross-linking reaction.

Applied to the surface of a catheter or guidewire, the lubricious coating maintains its lubricity despite the significant rubbing and abrasive force encountered during use, and in a preferred embodiment prevents or inhibits guidewire hang-up in the catheter lumen caused when agglomerations of blood and contrast increase the frictional resistance between the device surfaces and/or decrease the guidewire clearance. In the absence of the second photo cross-linker, the resulting coating would have a significant amount of the hydrophilic compound noncross-linked and only relatively weakly mechanically contained in the polymer network. Such coatings, which may be referred to as a semi-interpenetrating network (semi-IPN) coating, typically loose significant lubricity relatively quickly compared to the coating of the invention. By including a photo cross-linker specifically for the hydrophilic compound, the resulting coating of the invention preferably provides controlled cross-linking, and facilitates optimizing the curing of the coating to ultimately provide a desired amount of lubricity and durability. For example, the duration of the curing, and the amount of the second photo cross-linker relative to the amount of the hydrophilic compound are selected such that the assembled, sterilized device has a highly lubricious yet durable coating.

While not intending to be bound by theory, it is believed that the coating formulation of the invention allows for the hydrophilic compound to become chemically interlocked by cross-linking to itself (via the second photo cross-linker) to form a true interpenetrating network with the cross-linked polymer, without having the cross-linked polymer chemically (covalently) bond to the hydrophilic compound, for enhanced durability with good lubricity. Thus, it is believed that the hydrophilic compound network and the polymer network, which are chemically formed at the same time in the same mixture, are essentially permanently mechanically interlocked together. The coating is thus unlike a semi-IPN in which a noncross-linked hydrophilic compound is non-permanently mechanically intertwined/contained in a cross-linked polymer, and unlike a coating in which a matrix or underlayer polymer is used to chemically bond to the hydrophilic compound.

In one embodiment, the coating includes an adhesion promoter which improves the adhesion of the coating onto a polymeric or metal surface of the medical device. The adhesion promoter provides sufficiently strong adhesion onto the surface of the medical device, to thereby avoid the need for a reactive primer layer underneath the coating on the surface of the medical device.

A method of providing a lubricious coating for a medical device generally comprises preparing a solution mixture of a multifunctional monomer or polymer, a hydrophilic compound, one or more first initiators which preferentially cross-links the monomer or polymer relative to the hydrophilic compound, and one or more second initiators, different than the first initiator, which preferentially cross-links the hydrophilic compound relative to the monomer or polymer, and applying a coating of the solution mixture onto the surface of at least a section of the medical device. The coating of applied solution is then cured, such that the resulting lubricious coating is a network of the hydrophilic compound cross-linked to itself and interlocked with a network of the polymerized multifunctional monomer or polymer.

In one aspect of the present invention, the hydrophilic compound is a poylvinylpyrrolidone, the second photo cross-linker is a diazido compound, the multifunctional monomer or polymer is an acrylate oligomer, and the adhesion promoter is an acid functionalized acrylate. The resulting coating comprises an acrylate network of the polymerized multifunctional acrylate cross-linked to itself and to the cross-linked acid functionalized acrylate adhesion promoter, and a hydrophilic compound network of the polyvinylpyrrolidone cross-linked to itself by the diazido photo cross-linker, such that the hydrophilic compound network is interlocked with the acrylate network. The coated device can be e-beam or ethylene oxide (EtO) sterilized without significantly decreasing the lubricity or durability of the coating.

In one aspect of the present presentation, the hydrophilic compound is a polyethylene oxide, the multifunctional monomer or polymer is an acrylate oligomer, with one or more photoinitiators, and optionally includes a salt such as KBr. The resulting coating comprises an acrylate network of the polymerized multifunctional acrylate cross-linked to itself with noncross-linked polyethylene oxide, forming a semi-IPN. The coated device can be e-beam or ethylene oxide (EtO) sterilized without significantly decreasing the lubricity or durability of the coating.

The lubricious coating of the invention provides significant and long-lasting lubricity. As a result, when applied to a catheter and/or guidewire, the lubricious coating significantly reduces the frictional forces of the guidewire and the surface of a catheter shaft during advancement or retraction within a patient's body lumen for an extended period of time. These and other advantages of the invention will become more apparent from the following detailed description of the invention and the accompanying exemplary drawings.

DETAILED DESCRIPTION OF THE PREFERRED EMBODIMENTS

Figure 1:
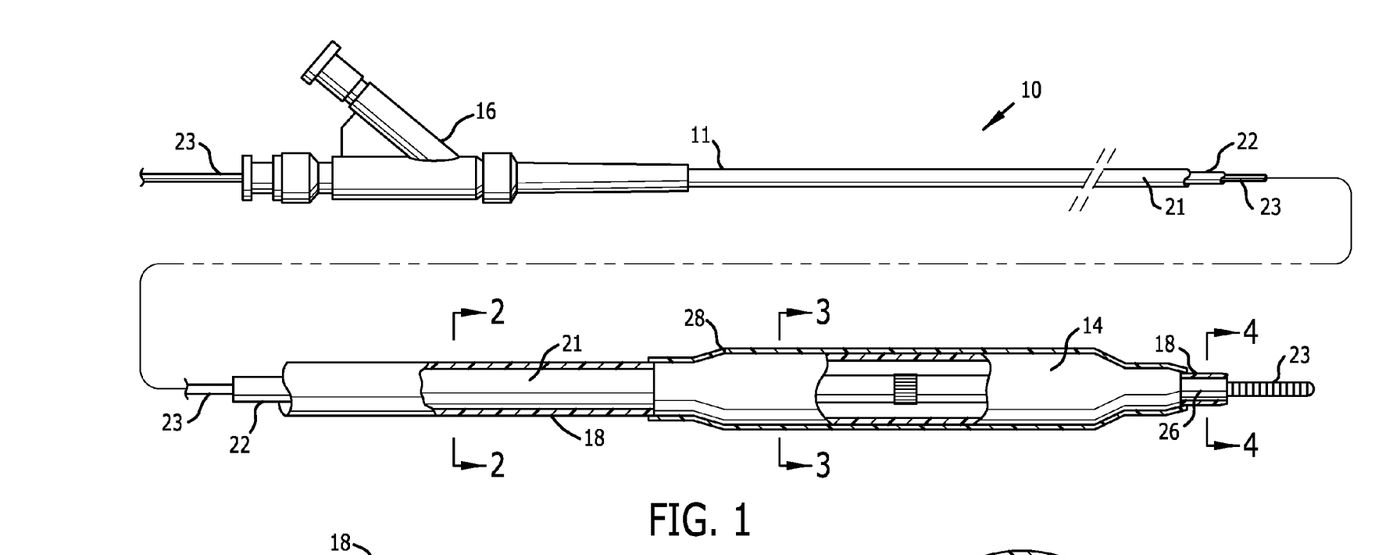
FIG. 1 is an elevational view, partially in section, of a balloon catheter having a lubricious coating of the invention on the catheter shaft.
Figure 2:
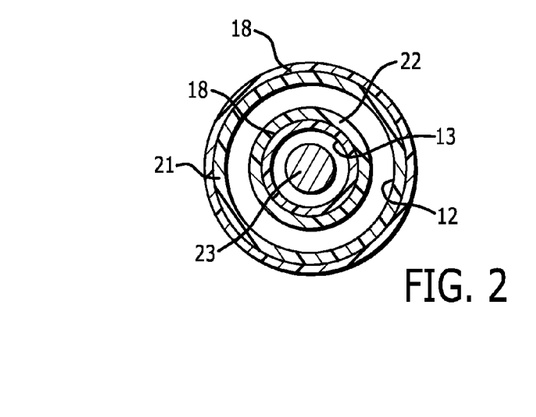
FIGS. 2, 3, and 4 are transverse cross sectional views of the catheter of FIG. 1, taken along lines 2-2, 3-3, and 4-4, respectively.
Figure 3:
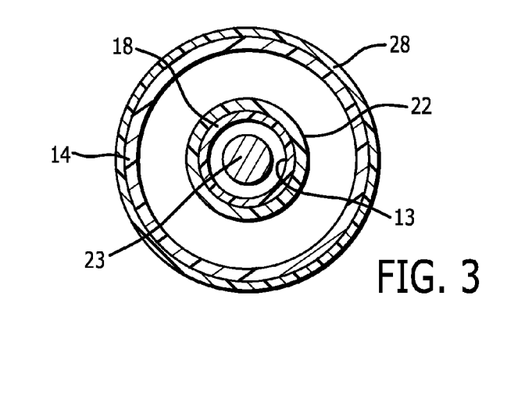

FIG. 1 illustrates one embodiment of the invention in which the medical device having a lubricious coating of the invention is a balloon catheter 10. The balloon catheter 10 generally comprises an elongated catheter shaft 11 having an inflation lumen 12 and a guidewire lumen 13 (see FIG. 2), and an inflatable balloon 14 on a distal shaft section with an interior in fluid communication with the inflation lumen. An adapter mounted 16 on the proximal end of the catheter shaft provides access to the guidewire lumen and connects to a source of inflation fluid (not shown) for inflating the balloon 14. As best shown in FIGS. 2 and 3, illustrating transverse cross sectional views of the catheter of FIG. 1 taken along lines 2-2 and 3-3, respectively, in the embodiment of FIG. 1, the shaft comprises an outer tubular member 21 having the inflation lumen 12 therein, and an inner tubular member 22 disposed in a lumen of the outer tubular member and having the guidewire lumen 13 therein configured to slidably receive a guidewire 23. The balloon 14 has a proximal skirt section sealingly secured to the distal end of the outer tubular member 21, and a distal skirt section sealingly secured to a distal end section of the inner tubular member 22, and an inflatable section therebetween. The catheter 10 can be advanced within a patient's body lumen, together with guidewire 23 or slidably advanced over previously introduced guidewire 23, to a desired location in the patient's body lumen, and the balloon 14 inflated to perform a medical procedure such as dilatation of a stenosis or expansion of a stent. When used as a stent delivery catheter, a stent 30 (see FIG. 5) is mounted on the balloon 14 for delivery and expansion within the patient's body lumen.

The catheter 10 has at least a section coated with a lubricious coating 18 of the invention, and more specifically has the lubricious coating 18 on at least a section of the shaft 11. In the embodiment of FIG. 1, the lubricious coating 18 is on the outer surface of the outer tubular member 21 (the outer lubricious coating and on a distal tip section 26 of the shaft 11. The outer lubricious coating 18 can be provided on various lengths of the catheter 10, including on the entire outer length of the catheter from the proximal adapter 16 to the distal-most end of the distal tip section 26 (i.e., along the outer surface of the outer tubular member 21, the balloon 14, and the distal tip section 26), or on a shorter length, such that the outer lubricious coating 18 typically extends from the distal-most end of the catheter, proximally for at least about 25 to about 40 cm. For example, in one embodiment, the lubricious coating 18 extends along a 25 to 40 cm portion of the catheter along the outer surface of the distal tip section 26, the balloon 14, and only a distal portion of the outer tubular member 21. If the catheter 10 is used for delivery of a stent, a section of the balloon may be masked during coating, so that the stent can be mounted on a noncoated section of the balloon for good stent retention. In the embodiment of FIG. 1, the outer surface of the balloon 14 has a coating 28, typically a lubricious coating, different than the lubricious coating 18 on the shaft 11, as discussed in more detail below. However, as discussed above, the balloon 14 can additionally or alternatively be coated with the lubricious coating 18.

Figure 4:
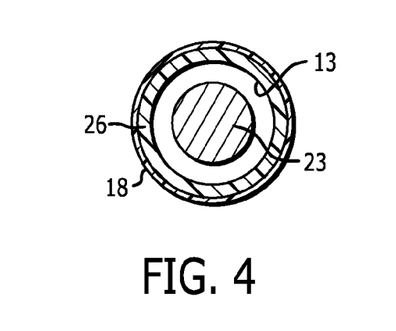
Figure 4A:
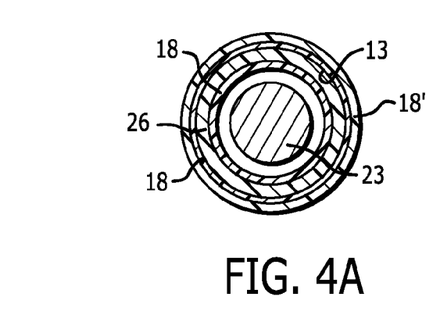
FIG. 4A is a transverse cross sectional view of an alternative embodiment, in which a catheter distal tip has the lubricious coating on an inner and outer surface of the distal tip, and has a less lubricious coating on the outer surface lubricious coating.

The distal tip section 26 of the shaft 11, formed by the distal end of the inner tubular member 22 and/or by a soft distal tip member secured to the distal end of the inner tubular member 22 and/or balloon proximal skirt, has the lubricious coating 18 on the outer surface thereof, as best shown in FIG. 4, illustrating a transverse cross section of the distal tip section 26 of the catheter 10 of FIG. 1, taken along line 4-4. FIG. 4a illustrates an alternative embodiment in which the lubricious coating 18 on the outer surface of the distal tip section 26 is further coated with a second, different lubricious coating, which in the embodiment of FIG. 4a is the same lubricious coating 28 that is on the balloon. The lubricious coating 18 is sufficiently durable to remain on the distal tip section 26 during assembly of the catheter 10, so that in one embodiment, the lubricious coating 18 is provided on the distal tip section 26 of the catheter prior to assembly and processing of the catheter 10, for example by dip coating or wiping on a distal tip member before it is attached to the inner member and/or balloon. After assembly of the catheter, the second lubricious coating 28 is applied on the balloon 14 and tip 26. The undercoat of lubricious coating 18 of the invention on the distal tip 26 is provided to minimize variations, and enhance the durability of the lubricity of the distal tip 26 of the fully assembled catheter, which improves the ability of the catheter to cross tight stenoses in the patient's body lumen. In a presently preferred embodiment, the hydrophilic coating applied to the fully assembled catheter is the interlocking network lubricious coating 18 discussed in more detail below, although in alternative embodiments a variety of suitable hydrophilic lubricious coatings including PEO or PVP based coatings can be applied to the catheter in accordance with a method of the invention.

Figure 5:
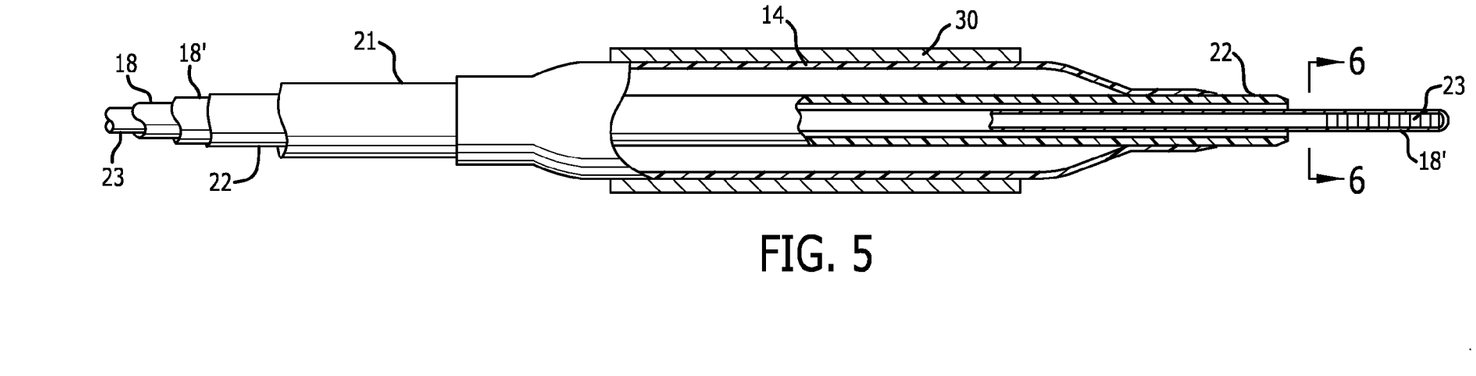
FIG. 5 illustrates a guidewire having a lubricious coating of the invention.

Although illustrated in the embodiment of FIG. 1 on the outer tubular member 21, inner tubular member 22, and distal tip section 26 of the catheter 10, it should be understood that the coating 18 can alternatively be applied to fewer areas of the catheter 10 such as just the outer tubular member 21, or to different areas of the catheter 10. Thus, the lubricious coating 18 of the invention can be applied to a variety of suitable locations on the catheter 10. Additionally, the lubricious coating 18 can be applied to a variety of suitable alternative medical devices. For example, FIG. 5 illustrates the lubricious coating 18 on guidewire 23. Guidewire 23 comprises a metallic core and coiled wire distal tip, and the coating 18 is preferably along at least a distal section of the guidewire including the floppy distal tip. Guidewire 23 having the lubricious coating 18 of the invention thereon preferably advances and retracts with very low friction force within the guidewire lumen of a catheter or in the vasculature.

Figure 6:
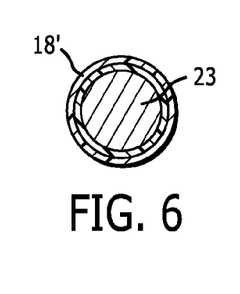
FIG. 6 is a transverse cross sectional view of the guidewire of FIG. 5, taken along line 6-6.

As best shown in FIG. 6, illustrating a transverse cross section of the guidewire of FIG. 5, in the embodiment of FIG. 5 the guidewire has a polymer layer 24 on an outer surface of the metallic core such that the lubricious coating 18 is on an outer surface of the guidewire polymer layer 24. In one embodiment, the polymer layer 24 is a polyurethane coating or layer on a stainless steel or NiTi core wire of the guidewire, although the polymer layer 24 can be formed of a variety of polymers including polyolefin, copolyamides, copolyesters or filled polyurethane. Fillers such as tungsten, barium, and bismuth and their compounds in general can be added to enhance radiopacity.

The lubricious coating 18, on catheter 10 and/or guidewire 23, comprises the cured reaction product of a solution mixture comprising a multifunctional monomer or polymer network-forming compound; a hydrophilic compound; one or more first cross-linkers for cross-linking the multifunctional monomer or polymer, which preferentially cross-links the multifunctional monomer or polymer relative to the hydrophilic compound; and one or more second cross-linkers, different than the first cross-linkers, for cross-linking the hydrophilic compound, which preferentially cross-links the hydrophilic compound relative to the multifunctional monomer or polymer. The resulting cured coating on the medical device is a network of the hydrophilic compound cross-linked or non cross-linked to itself and interlocked with a network of the cross-linked polymerized multifunctional monomer or polymer.

The multifunctional network-forming compound is preferably a triacrylate oligomer such as a high molecular weight ethoxylated trimethylol propane triacrylate (ETMPTA) (e.g., PHOTOMER® 4158, available from Cognis) or trimethylol propane triacrylate (TMPTA, available from Sigma Aldrich.) The ETMPTA oligomer polymerizes and cross-links during curing to form a network of cross-linked ETMPTA. Alternative cross-linkable polymers (formed from alternative multifunctional monomers or polymers) for forming an interlocking network with the hydrophilic compound include urethane, epoxy, polyester acrylates, and unsaturated polyesters, although a triacrylate, and particularly ETMPTA and TMPTA, is preferred due to its enhanced hydrophilic property, and compatibility with common solvents for good manufacturability. Less preferred is a methacrylate due to the slow reaction and sensitivity to oxygen.

Preferred cross-linkers are photosensitive molecules (photo cross-linkers). Specifically, in the embodiment in which the multifunctional oligomer is a triacrylate, the solution mixture preferably includes mixed first photoinitiators including benozophenone, and a benzil dimethyl ketal such as 2,2-dimethoxy-2-phenyl acetophenone (PHOTOMER® 51, available from Cognis) for photocuring the triacrylate. A variety of mixed first photoinitiators are typically provided, which work by different mechanisms to initiate polymerization and cross-linking of the triacrylate (and acrylates in general) as is generally known. For example, upon irradiation, PHOTOMER® 51 undergoes a unimolecular bond cleavage to yield free radicals, while the benezophenone undergoes a bimolecular reaction in the presence of alcohol in which hydrogen abstraction creates hydroxyl (or ketal-type) radicals. However, a variety of suitable first photo cross-linkers can be used which preferentially cross-link the multifunctional polymerized monomer or polymer (e.g., triacrylate oligomer). For example, alternative photoinitiators for cross-linking the triacrylate include 1-hydroxy-cyclohexyl-phenyl-ketone, and 2-hydroxy-2-methyl-1-phenyl-1-propanone, although the preferred photoinitiators provide superior manufacturability due at least in part to good solubility. Ultraviolet, as opposed to visible light, photoinitiation is preferred for faster curing time.

In one aspect of the present invention, a presently preferred hydrophilic compound is a polyvinylpyrrolidone (PVP, (poly (N-vinyl-2-pyrrolidone)), which, when in combination with the second photo cross-linker such as a diazidostilbene (DAS) or derivative thereof, cross-links during curing to form a network of cross-linked PVP. Presently preferred PVPs include PVP K-90 and PVP K-120, available for example from ISP Chemicals, Inc., the K number being significant as it is related to the molecular weight of the PVP. Preferred cross-linkable PVPs have a relatively high molecular weight of greater than about 1,000,000 g/mole for cross-linking to form the desired (lubricious) network. A presently preferred diazidostilbene for preferentially cross-linking the PVP is 4,4'-diazido-2,2'-stilbene disulfonic acid disodium salt. Other possible diazido based second photo cross-linkers that could be used include diazidostilbene derivatives including those set forth in U.S. Pat. No. 5,041,570, the Summary and Detailed Description of the Invention of which are hereby incorporated by reference. Upon irradiation, DAS (a photo cross-linking agent) forms a highly reactive intermediate nitrene group on both ends, and then the nitrene groups on the DAS will react with PVP to form the cross-linked network of PVP. In accordance with the invention, the DAS preferentially cross-links the PVP relative to the multifunctional monomer or polymer network-forming compound (e.g., the triacrylate). That is, the DAS cross-links PVP polymer chains together, substantially without cross-linking the polymer chains of the multifunctional polymerized monomer or polymer. Similarly, the first photo cross-linkers are not expected to cross-link the hydrophilic compound (PVP) of the coating of the invention. Additionally, curing the coating does not cross-link, graft or otherwise chemically bond the hydrophilic compound to the polymerized monomer or polymer, or to the substrate. Thus, although a variety of hydrophilic compounds are well known for use in lubricious coatings for medical devices, in the coating of the invention the hydrophilic compound has a specific initiator which can be added to the solution mixture to preferentially cross-link the hydrophilic compound to itself to a desired degree. Alternative hydrophilic compound-second photo cross-linker combinations that can be used in the coating of the invention include the combination of polyethylene glycol diacrylates (PEGDA) and the photoinitiator 2,2-dimethoxy-2-phenylacetophenone.

The amount of the second cross-linkers provided in the solution mixture relative to the amount of the hydrophilic compound, and the duration of the curing is sufficient to form a three dimensional cross-linked network of the hydrophilic compound, although the hydrophilic compound is cross-linked to a greater or less degree depending on the desired performance characteristics of the lubricious coating 18. The control provided by the invention over the cross-linking of the hydrophilic compound facilitates creating a desired lubricity and durability which can be tailored for different applications. Thus, PVP that is part of the network in lubricious coating 18 has a greater or lesser degree of cross-linking. Additionally, some noncross-linked hydrophilic compound (i.e., PVP that is not cross-linked and thus not part of the network) or a noncross-linked secondary hydrophilic compound such as PEO are present in the lubricious coating in some embodiments, for enhanced lubricity at the potential expense of durability. Specifically, network lubricious coatings in which durability and not lubricity was at issue would cross-link the hydrophilic compounds to a greater degree to maximize the durability of the coating at the expense of the lubricity, which may be acceptable in some applications. Additionally, because the cross-linking of the hydrophilic compound is more readily controllable in the lubricious coating of the invention, the amount of cross-linking caused by initially photo-curing the coating on the device can be tailored to compensate for any additional cross-linking that may occur later, as for example when sterilizing the coated device by e-beam or EtO sterilization causes further cross-linking of the coating. In one embodiment, the coated device is e-beam sterilized, and the method of coating the device involves (UV) curing the coating on the device for a relatively short duration which is insufficient to cross-link the compounds to the desired degree (e.g., as determined by performance testing of the coated medical device), and subsequently e-beam sterilizing the coated device such that the compounds further cross-link to the desired degree. Similarly, the amount of photo cross-linkers in the coating can be limited to control the amount of cross-linking caused by the photo-curing.

The solution mixture is formed by combining the multifunctional monomer or polymer, one or more hydrophilic compounds, one or more first cross-linkers, and optionally one or more second cross-linkers together in a single solution (the compounds typically having been first dissolved in a suitable solvent before combining to form the single solution). The solution mixture is then applied to the surface of the catheter shaft 11 and/or guidewire 23, and it can be applied to the device using a variety of suitable methods including dipping, spraying, wiping the solution on the surface of the catheter or guidewire. The coating is then typically dried on the device before the curing, and the resulting cured coating has the substantially uniform composition provided by the interlocked networks in a single layer. In one embodiment, an adhesion promoting primer is first coated onto the device and cured, and then the lubricious coating solution mixture is applied onto the cured primer. The cured coating 18 has to be hydrated to render it lubricious for use in a medical procedure. The water induction time, i.e., the time required to hydrate the coating, varies depending on the coating formulation. Thus, the terminology "lubricious coating" as used herein should be understood to refer to the finished coating on the device, either before or after the hydrophilic compound is hydrated to render the coating lubricious for use.

In one embodiment, the solution mixture includes an adhesion promoter comprising an acid functionalized acrylate which adheres to a surface of the medical device to improve adhesion of the lubricious coating 18 on the medical device. The preferred adhesion promoter bonds to the surface of the substrate (e.g., the polymer surface of the catheter shaft or the guidewire) and also cross-links to the multifunctional polymerized monomer or polymer. Thus, the first initiators preferably cross-link the adhesion promoter, such that the adhesion promoter is cross-linked to itself and to the cross-linked polymerized multifunctional monomer or polymer in the cured lubricious coating. A presently preferred adhesion promoter is PHOTOMER® 4173, an acid functionalized monoacrylate from Cognis, which bonds to a polymeric (and particularly a polyurethane) substrate layer. Alternative adhesion promoters which could be used include the acid functionalized acrylates PHOTOMER® 4703 and 4846 from Cognis. The adhesion promoter is generally about 0.2% to about 20%, more specifically about 1% to about 2%, by weight of the solution mixture. A reactive primer layer on the device, such as these acid functionalized adhesion promoters (plus a photoinitiator) or other primer compounds such as a urethane acrylate, could additionally or alternatively be used to improve adhesion. With or without the adhesion promoter, the coating 18 of the invention adheres to the surface of the device without requiring that the hydrophilic compound is functionalized or otherwise made to reactively chemically bond to a matrix or substrate polymer.

In one embodiment, the solution mixture includes a secondary hydrophilic compound such as polyethylene oxide (PEO) which is different than the network forming hydrophilic compound (e.g., PVP). The secondary hydrophilic compound is substantially noncross-linked in the lubricious coating. Thus, an initiator which preferentially cross-links the secondary hydrophilic compound is not included in the solution mixture, and curing the coating produces relatively little or no cross-linking of the secondary hydrophilic compound. As a result of being substantially noncross-linked, the secondary hydrophilic compound preferably provides a coating which is, at least initially, more lubricious and/or which has a decreased water induction time (i.e., a quicker response to a hydration procedure). For example, a substantially noncross-linked hydrophilic compound such as polyethylene oxide (PEO) in the coating hydrates relatively quickly. Specifically, combining the first hydrophilic compound such as PVP with the secondary hydrophilic compound such as PEO or polyacrylamide provides a coating that preferably has an improved, fast water induction time after sterilization by e-beam or EtO treatment. Noncross-linked PEO or polyacrylamide preferably compensates for an increase in water induction time of the lubricious coating due to both e-beam and EtO sterilization. A variety of suitable hydrophilic compounds can be used as the secondary hydrophilic compound including PEO, polyacrylamide-co-acrylic acid and polyacrylamide, a cellulose such as hydroxyl propyl cellulose (HPMC). In one embodiment, a relatively small amount of the secondary hydrophilic compound is present in the coating. For example, in one embodiment, the secondary hydrophilic compound is only about 5% by weight of the amount of PVP in the lubricious coating.

In one embodiment, the solution mixture includes a dissolvable ionic compound (i.e., a salt) such as sodium chloride or potassium bromide, and the resulting cured lubricious coating has the salt contained (dissolvably) therein at least prior to the hydration procedure used to hydrate the coating for use. The water induction time is believed to decreased relative to the coating without the salt as a result of the presence of the salt in the cured coating.

In one embodiment, the cured lubricious coating has a therapeutic or diagnostic agent. For example, an agent added to the solution mixture is releasably contained in the cured coating such that as the cured coating swells (hydrates) during use, the agent will elute therefrom. The cured lubricious coating can be provided with a variety of agents. Anti-platelet agents, anti-thrombogenic agents, anti-coagulant agents, anti-inflammatory agents, vasodilator agents, and the like are particularly preferred for adding to the lubricious coating on the balloon 14, outer member 21, guidewire 23, and/or within the guidewire lumen 13 of the catheter shaft 11. A relatively small molecule agent such as aspirin (acetylsalicyclic acid; acetolsal) is particularly desirable in the lubricious coating because its relatively quick elution time from the lubricious coating provides a concentrated quick dose of the aspirin during the initial introduction and advancement of the catheter and/or guidewire in the patient's body lumen. Although controlled, longer term elution of agents from medical device coatings is a goal of many of prior art coatings, relatively quick, uncontrolled elution of the aspirin from the lubricious coating of the invention is desirable. The concentrated release of the aspirin from the lubricious coating upon hydration of the coating provides an anti-platelet affect during positioning of the catheter in the body lumen, which further reduces guidewire hang-up in the catheter guidewire lumen. Although aspirin has a small molecular weight (e.g., 180 g/mol), alternative agents with larger molecular weights than aspirin can alternatively be used in a coating of the invention, such as Hirudin (about 7,000 g/mol) or Heparin (about 12,000 to about 15,000 g/mol).

The lubricious coating of the invention can be provided with a variety of suitable agents (small or large molecule agents) including anti-restenosis agents, and anti-inflammatory, anti-coagulating, or pro-healing drugs. The agent is typically provided by adding it into the solution mixture prior to application onto the device, which is a preferred method due to the good manufacturability, control over the amount and location of the agent on the device, and minimal disruption of the lubricity of the coating. Less preferred methods include swelling the cured coating on the device with a solution of the agent prior to use.

In the embodiment illustrated in FIG. 1, the coating 28 on the balloon 14 is different than the lubricious coating 18 on the shaft. For example, the coating 28 on the balloon may be a lubricious coating which has less lubricity or may contain a different therapeutic agent than the coating on the shaft. In alternative embodiments as discussed above, the same lubricious coating 18 on the shaft 11 is provided on the balloon 14.

In one embodiment, the agent delivery lubricious coating 28 on the balloon is the embodiment of the interlocking network lubricious coating described above having the noncross-linked secondary hydrophilic compound added thereto which provides a quick water induction (e.g., noncross-linked PEO in the interlocking network of cross-linked PVP and cross-linked triacrylate). As discussed above, the agent is preferably added to the solution mixture of the lubricious coating prior to coating of the balloon. The catheter and balloon having the agent delivery lubricious coating thereon is then folded or otherwise configured into a low profile configuration for advancement within the patient's body lumen.

In one embodiment, coating 28 on the balloon is a less lubricious coating than the lubricious coating 18 on the shaft, to prevent or inhibit the inflated balloon from slipping out of the desired treatment location in the patient's body lumen ("watermelon seeding"). Such a medical device is said to have a "coating gradient" in that the lubricity of the coating varies from its distal end to its proximal end. There are a number of alternate approaches to making the coating 28 on the balloon as a less lubricious coating than the lubricious coating 18 on the shaft. For example, a more dilute concentration solution of the same ingredients can be applied on the balloon after the same or more concentrated solution is applied over the shaft and balloon. As another example, a coating comprised of the solution incorporating one hydrophilic polymer (for example PEO) can be applied on the balloon, while a coating comprised of the solution incorporating a different hydrophilic polymer (for example PVP) can be applied on the shaft. As another example, the lubricious coating 28 can comprise the reaction product of a solution mixture of a binding multifunctional oligomer (or monomer or higher molecular weight polymer), a photo cross-linker for cross-linking the binding oligomer, and a hydrophilic compound without a photo cross-linker for preferentially crosslinking the hydrophilic compound of the less lubricious coating. The coating 28 on the balloon can thus be formed of the same component compounds as the coating 18 on the shaft but without the second photo cross-linkers, to result in a less lubricious coating. Alternatively, cure time can be adjusted to result in a less lubricious coating on the balloon. Alternatively, the first hydrophilic coating and the second hydrophilic coating may have different concentration of solids or % solid, second coating having less hydrophilic polymer. Although coating 28 is illustrated extending along the entire length of the balloon from the proximal to the distal ends of the balloon, it should be understood that in alternative embodiments, the coating 28 can extend along a shorter length of the balloon or beyond the ends of the balloon.

Figure 7:
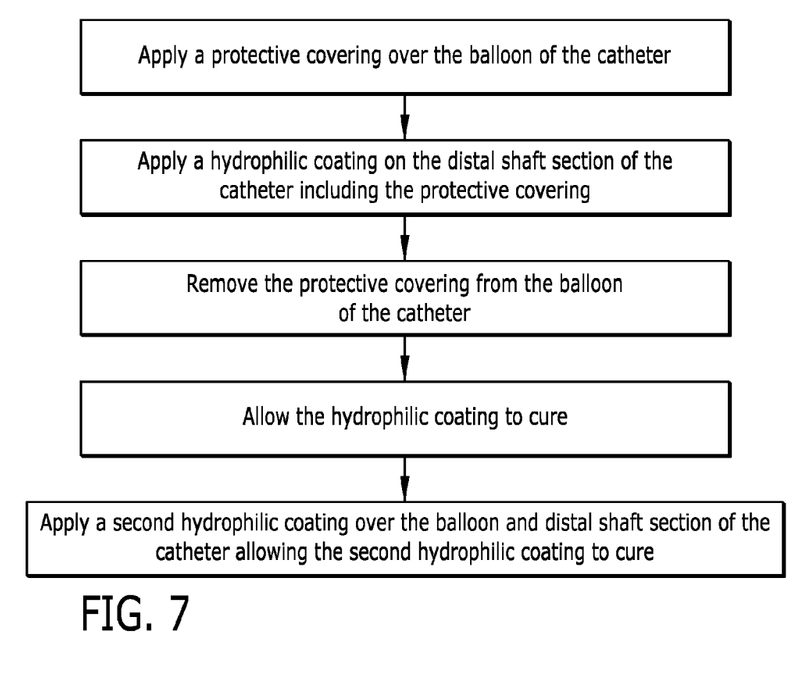
FIG. 7 is a flow chart showing one method for coating a balloon catheter in accordance with the present invention.

Another method for forming a "coating gradient" on the balloon catheter is disclosed in FIG. 7. For example, the balloon 14 of the catheter could have a protective covering initially placed over it to prevent the balloon from receiving a first hydrophilic coating. For example, the protective coating can be, for example, an elastomeric sheath tubing which is placed over the balloon when the balloon is placed in an inflated condition. Alternatively, the protective coating could be placed over the balloon 14 while the balloon remains in a collapsed position. For example, if the balloon is initially in an inflated condition, the balloon could be placed in a deflated condition to allow the protective covering to be more easily removed. After the first hydrophilic coating such as Formulation A in the Table 1 is applied to the catheter and UV cured, the protective covering is removed. It should be appreciated that the entire length of the catheter 10 does not necessarily have to be coated with a lubricious coating since a good portion of the catheter 10 never enters the patient during the procedure and hence need not be lubricious. Lubricity can be confined to the areas of the catheter 10 which actually enters the patient.

The following example illustrates a solution mixture for a lubricious coating 18 of the invention for forming a "coating gradient" on the balloon catheter.

TABLE 1

| Chemical | Specific Weight % (Formulation A) | General Weight % Range Formulations |
|---|---|---|
| Isopropanol (IPA) | 84.770 | about 80 to about 90 |
| Water | 14.677 | about 10 to about 20 |
| PEO | 0.475 | about 0.2 to about 2.0 |

TABLE 1-continued

| Chemical | Specific Weight % (Formulation A) | General Weight % Range Formulations |
|---|---|---|
| Hydroxycyclohexyl phenyl ketone | 0.001 | about 0.0005 to about 0.0025 |
| Benzophenone | 0.001 | about 0.0005 to about 0.0025 |
| TMPTA | 0.053 | about 0.01 to about 0.10 |
| KBr | 0.024 | about 0.01 to about 0.05 |

Figure 2A:
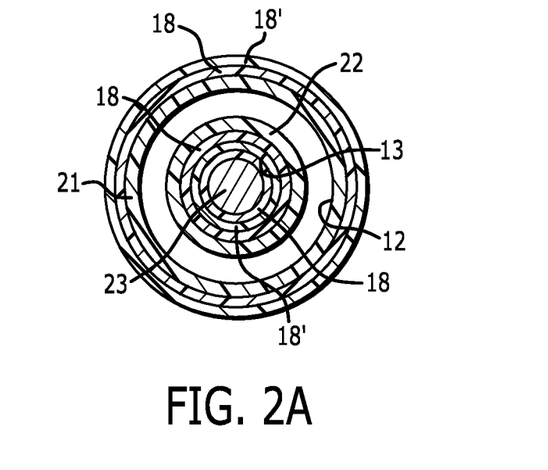
FIG. 2A is a transverse cross sectional view of an alternative embodiment of a balloon catheter and guide wire each having a particular lubricious coating of the invention.
Figure 3A:
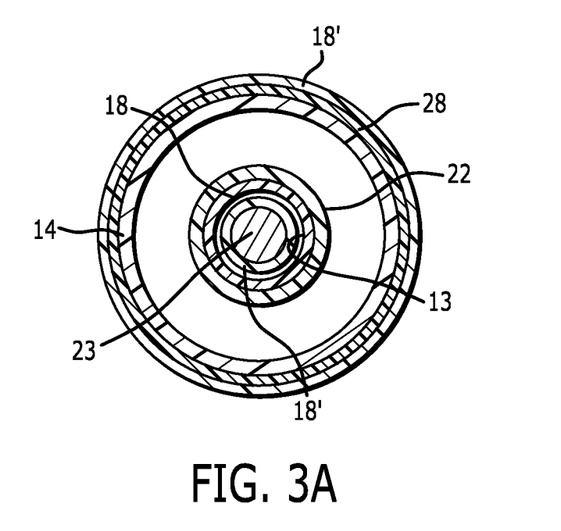
FIG. 3A is a transverse cross sectional view of an alternative embodiment of a balloon catheter and guide wire each having a particular lubricious coating of the invention.
Figure 4B:
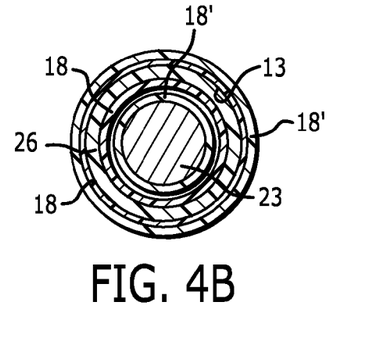
FIG. 4B is a transverse cross sectional view of an alternative embodiment of a balloon catheter and guide wire each having a particular lubricious coating of the invention.

Next, after the protective covering has been removed, a second hydrophilic coating could be applied to the catheter. In this method, the balloon will only have a single layer of hydrophilic coating opposed to the remainder of the catheter which will have a double coating of hydrophilic coating. FIG. 2A shows a cross sectional of the catheter along line 2-2. As can be seen in this figure, a second hydrophilic coating 18' is shown disposed over the first hydrophilic coating 18 in the region proximal to the balloon 14. Referring now to FIG. 3A, the cross sectional view of the balloon region of the catheter is shown. As can be seen in FIGS. 3A and 4B, the second hydrophilic coating 18" is shown disposed on the outer surface of the balloon 14. The single hydrophilic coating 18' can extend along the distal end of the inner tubular member 22 as well. Accordingly, the balloon 14 will not be as lubricious as the region of the catheter located proximal to the balloon 14 since that region has a double coating of the hydrophilic mixture. In this manner, a coating gradient can be applied to the catheter which can address the problems associated with "watermelon seeding."

As another example, a coating comprised of the solution incorporating a hydrophilic polymer, for example PEO, can be applied as the first coating 18 and the second coating 18' can be the same polymer. Other hydrophilic polymers, for example PVP, could also be used as the first coating 18 and second coating 18'. Other hydrophilic coatings like the ones disclosed herein could be used as well as others well known in the art. Alternatively, the first coating 18 could be made from a different hydrophilic material than the second coating 18'. However, the different first and second coatings 18 and 18' should be somewhat compatible since the second coating 18' will be deposited upon the first coating 18.

Figure 8:
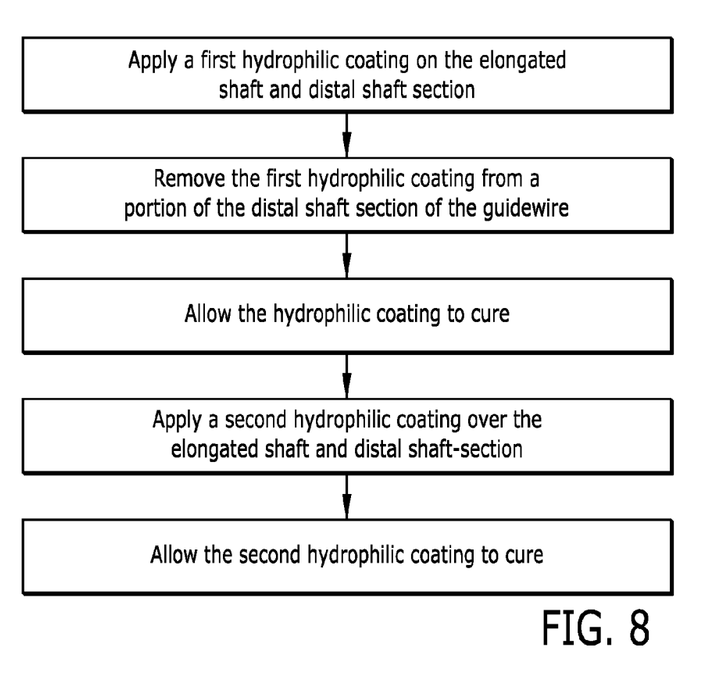
FIG. 8 is a flow chart showing one method for coating a guide wire in accordance with the present invention.

Referring now to FIG. 8, a method for creating a coating gradient on the guidewire 23 is disclosed. This method creates a guidewire having less lubricity at the distal end portion of the guidewire 23 than the shaft portion which extends proximally away from the distal end section. The method includes the application of a first hydrophilic coating on the elongated shaft and distal shaft section of the guidewire. Next, the first hydrophilic coating is removed from a portion of the distal shaft section of the guidewire. This first hydrophilic coating is then allowed to cure. For example, the first coating could be subjected to an ultraviolet source that helps to cure the material. For example, coating on approximately 5-10 cm of the distal end section of the guidewire 23 could be removed. In one process, the first hydrophilic coating is removed from the portion of the distal shaft section by placing the portion of the distal shaft section in an isopropanol bath which is agitated ultrasonically.

After the first coating has been removed from a portion of the distal shaft section of the guidewire, a second hydrophillic coating can be applied to the elongated shaft and distal shaft section of the guidewire. Thereafter, the second hydrophilic coating can be allowed to cure. For example, the second coating also could be subjected to an ultraviolet source that helps to cure the material.

Figure 5A:
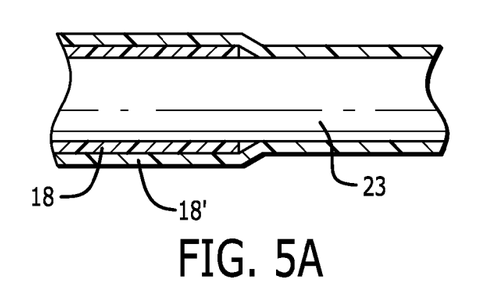
FIG. 5A is a side elevational view partially in cross section showing the transition region of the coatings on the guide wire of FIG. 5.
Figure 6A:
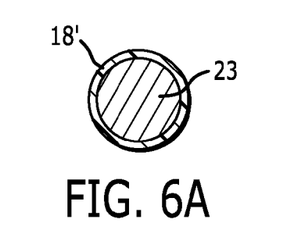
FIG. 6A is a transverse cross sectional view of an alternative embodiment of a balloon catheter and guide wire each having a particular lubricious coating of the invention.

Referring now to FIGS. 2A, 5A and 6A, the different coatings that extend along the length of the guidewire 23 is shown. As can be seen in FIG. 2A, the guide wire 23 includes the first hydrophilic coating 18 and the second hydrophilic coating 18' which provides for greater lubricity along the length of the guidewire extending proximally from the distal end section. FIG. 5A shows the transition region where the two coatings 18 and 18' of the guide wire 23 transition to a single layer 18'. FIG. 6A shows the single coating 18 which extends along the distal end section which is not quite as lubricious as the remainder of the guidewire. In this fashion, a coating gradient can be created on the guidewire 23.

As another example, a coating for use on the guidewire comprises of the solution incorporating a hydrophilic polymer, for example PVP, could be used as the first coating 18 and second coating 18'. Such a coating should include a photo cross-linker if the coating is to be cured via an ultraviolet source. Other hydrophilic coatings like the ones disclosed herein could be used as well as others well known in the art. Alternatively, the first coating 18 could be made from a different hydrophilic material than the second coating 18'. However, the different first and second coatings 18 and 18' should be somewhat compatible since the second coating 18' will be deposited upon the first coating 18.

The following example illustrates a solution mixture for a lubricious coating as the first coating 18 and second coating 18' of the invention for a coating for use on the guidewire comprising of the solution incorporating a hydrophilic polymer. In addition to the specific formulation (with the amount of each component expressed as a weight percent of the solution mixture) used in the following example, the Table also give example solution weight percent ranges for the components which can be used in making coatings of the invention

TABLE 2

| Chemical | Specific Weight % (Formulation B) | General Weight % Range Formulations |
|---|---|---|
| Ethanol | 79.63 | about 60 to about 80 |
| Isopropanol (IPA) | 5.53 | about 2 to about 10 |
| Water | 5.53 | about 2 to about 10 |
| PVP K-90 | 6.30 | about 2 to about 10 |
| PEO | 0 | about 0 to about 10 |
| PHOTOMER ® 4173 | 1.02 | about 0 to about 5 |
| PHOTOMER ® 4158 (ETMPTA) | 1.89 | about 1 to about 5 |
| PHOTOMER ® 51 | 0.019 | about 0.01 to about 0.05 |
| Benzophenone | 0.019 | about 0.01 to about 0.05 |
| 4,4'-diazido-2,2-stilbenedisulfonic acid disodium salt hydrate | 0.063 | about 0.01 to about 0.25 |

The dimensions of catheter 10 are determined largely by the size of the balloon and guidewire to be employed, the catheter type, and the size of the artery or other body lumen through which the catheter must pass or the size of the stent being delivered. Typically, the outer tubular member 21 has an outer diameter of about 0.025 to about 0.04 inch (0.064 to 0.10 cm), usually about 0.037 inch (0.094 cm), and the wall thickness of the outer tubular member 21 can vary from about 0.002 to about 0.008 inch (0.0051 to 0.02 cm), typically about 0.003 to 0.005 inch (0.0076 to 0.013 cm). The inner tubular member 22 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 14 has a length about 0.8 cm to about 6 cm, and an inflated working diameter of about 2 mm to about 10 mm. The guidewire 23 typically has length of about 190 to about 300 cm, and an outer diameter of about 0.010 to about 0.035 inch.

The various catheter components may be joined using conventional bonding methods such as by fusion bonding or use of adhesives. Although the shaft 11 is illustrated as having an inner and outer tubular member, a variety of suitable shaft configurations may be used including a dual lumen extruded shaft having a side-by-side lumens extruded therein. Additionally, although the embodiment illustrated in FIG. 1 is an over-the-wire type balloon catheter having a guidewire lumen extending the full length of the catheter, it should be understood that the coating 18 and 18' of the invention can be used with a variety of suitable catheters including guiding catheters having a device lumen configured for delivering catheters or other devices, or rapid-exchange type balloon catheters having a guidewire proximal port spaced distally from the proximal end of the catheter shaft.

While the present invention is described herein in terms of certain preferred embodiments, those skilled in the art will recognize that various modifications and improvements may be made to the invention without departing from the scope thereof. For example, although discussed primarily in terms of a coating on a catheter shaft or guidewire, it should be understood that the lubricious coating 18 and 18' of the invention can be provided on a variety of medical devices, and is particularly suitable for use on surfaces encountering significant rubbing or abrasive forces during use or assembly and processing. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. A method of providing a lubricious coating for a balloon catheter having an elongated catheter shaft and a balloon on a distal shaft section, the method comprising:
   applying a protective covering over the balloon of the catheter;
   applying a first hydrophilic coating on the distal section of the catheter including the protective covering section;
   removing the protective covering from the balloon of the catheter;
   allowing the first hydrophilic coating to cure;
   applying a second hydrophilic coating over the distal shaft section of the catheter after the protective covering has been removed from the balloon; and
   allowing the second hydrophilic coating to cure.

2. The method of claim 1 wherein the first hydrophilic coating is cured using an ultraviolet source.

3. The method of claim 1 wherein the second hydrophilic coating is cured using an ultraviolet source.

4. The method of claim 1 wherein the first hydrophilic coating is made from the same solution mixture as is the second hydrophilic coating.

5. The method of claim 1 wherein the first hydrophilic coating and the second hydrophilic coating have different concentration of solids.

6. The method of claim 1 wherein the balloon is in an inflated condition when the protective covering is being applied to the balloon.

7. The method of claim 6 wherein the protective covering is removed from the balloon by placing the balloon section in a deflated condition.

8. The method of claim 1 wherein the protective coating is an elastomeric sheath tubing.

9. The method of claim 8 wherein the elastomeric sheath tubing expands when the balloon is in the inflated condition.

10. The method of claim 9 wherein the elastomeric sheath tubing contracts when the balloon section is in the deflated condition.

11. The method of claim 1 wherein the first and second coatings are made from a solution incorporating a hydrophilic polymer.

12. The method of claim 11 wherein the first and second coatings include polyethylene oxide.

13. The method of claim 12 wherein the first and second coatings are made from a substantially non-cross-linked hydrophilic compound.

14. The method of claim 11 wherein the first and second coatings include polyvinylpyrrolidone.

15. The method of claim 14 wherein the first and second coatings are made from a substantially cross-linked hydrophilic compound.

16. A method of providing a lubricious coating for a guidewire having an elongated shaft and a distal shaft section, the method comprising:
   applying a first hydrophilic coating on the elongated shaft and distal shaft section;
   removing the first hydrophilic coating from a portion of the distal shaft section of the guidewire;
   allowing the first hydrophilic coating to cure;
   applying a second hydrophilic coating over the elongated shaft and distal shaft section; and
   allowing the second hydrophilic coating to cure.

17. The method of claim 16 wherein the first hydrophilic coating is cured using an ultraviolet source.

18. The method of claim 16 wherein the second hydrophilic coating is cured using an ultraviolet source.

19. The method of claim 16 wherein the first hydrophilic coating is made from the same solution mixture as is the second hydrophilic coating.

20. The method of claim 16 wherein the first hydrophilic coating and the second hydrophilic coating have different concentration of solids.

21. The method of claim 16 wherein the first hydrophilic coating is removed from the portion of the distal shaft section by placing the portion of the distal shaft section in an isopropanol bath.

22. The method of claim 21 wherein the isopropanol bath is agitated ultrasonically when the portion of the distal shaft section is placed therein.

23. The method of claim 16 wherein the first and second coatings are made from a solution incorporating a hydrophilic polymer.

24. The method of claim 23 wherein the hydrophilic polymer is a polyvinylpyrrolidone.

25. The method of claim 23 wherein the hydrophilic polymer is a polyethylene oxide.

* * * * *